United States Patent [19]
Willson

[11] Patent Number: 6,018,562
[45] Date of Patent: Jan. 25, 2000

[54] APPARATUS AND METHOD FOR AUTOMATIC RECOGNITION OF CONCEALED OBJECTS USING MULTIPLE ENERGY COMPUTED TOMOGRAPHY

[75] Inventor: Paul D. Willson, Rockaway, N.J.

[73] Assignee: The United States of America as represented by the Secretary of the Army, Washington, D.C.

[21] Appl. No.: 09/087,694

[22] Filed: May 22, 1998

Related U.S. Application Data

[63] Continuation-in-part of application No. 08/968,799, Nov. 17, 1997, which is a continuation of application No. 08/591,839, Jan. 25, 1996, abandoned
[60] Provisional application No. 60/006,670, Nov. 13, 1995.
[51] Int. Cl.$^7$ .................................................. G01N 23/16
[52] U.S. Cl. .................................................. 378/9; 378/57
[58] Field of Search ........................................ 378/5, 9, 57

[56] References Cited

U.S. PATENT DOCUMENTS

| | | | |
|---|---|---|---|
| 4,274,005 | 6/1981 | Yamamura et al. | 378/9 |
| 4,651,005 | 3/1987 | Baba et al. | 378/5 |
| 5,175,756 | 12/1992 | Pomgratz et al. | 378/88 |
| 5,524,133 | 6/1996 | Neale et al. | 378/53 |

OTHER PUBLICATIONS

R.M. Wallingford, et al., "Application of Two–Dimensional Matched Filters to X–Ray Radiographic Flaw Detection and Enhancement", Revs of Prog. in QNDE, vol. 11, 1992, pp. 879–886.

M.S. Chackalackal et al., "NDE X–Ray Image Analysis Using Mathematical Morphology", Rev. of Prog. in QNDE, vol. 9, 1990, pp. 721–728.

M.S. Chackalackal et al., "NDE X–Ray Image Analysis Using Mathematical Morphology", Rev. of Prog. in QNDE, vol. 9, 1990, pp. 887–894.

"Standard Guide for Computed Tomography (CT) Imaging," ASTM, Designation E 1441–93, Apr. 1993.

Andersen, Anders H., "Algebraic Reconstruction in CT from Limited Views", IEEE Transactions on medical Imaging, vol. 8, No. 1, pp. 50–55, Mar. 1989.

N.J. Dusaussoy et al., "The Extended MENT Algorithm: A Promising Reconstruction Algorithm for Computerized Tomography," IEEE, 1989, pp. 1460–1463.

*Primary Examiner*—David P. Porta
*Attorney, Agent, or Firm*—John Moran; Michael Sachs

[57] ABSTRACT

An apparatus and method for automatic recognition and identification of concealed objects and features thereof, such as contraband in baggage or defects in articles of manufacture, is disclosed. The apparatus uses multiple energy X-ray scanning to identify targets with a spectral response corresponding to a known response of targets of interest. Detection sensitivity for both automatic detection and manual inspection are improved through the multiple-energy, multispectral technique. Multichannel processing is used to achieve high throughput capability. Target identification may be verified through further analysis of such attributes as shape, texture, and context of the scan data. The apparatus uses a statistical analysis to predict the confidence level of a particular target identification. A radiograph, CT image, or both may be reconstructed and displayed on a computer monitor for visual analysis by an operator. Finally, the apparatus may receive and store input from the operator for use in subsequent target identification.

3 Claims, 12 Drawing Sheets

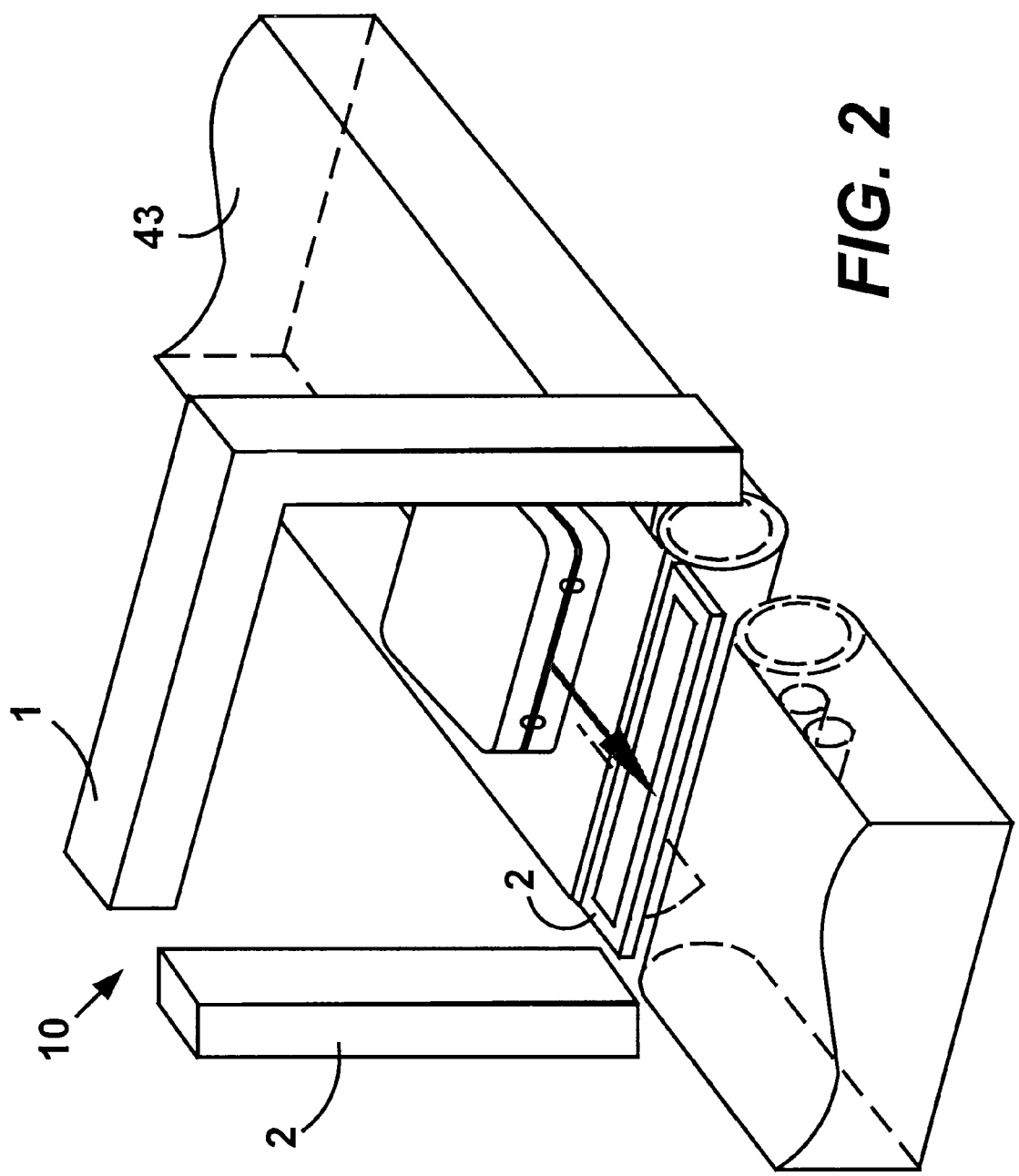

APPARATUS AND METHOD FOR AUTOMATIC RECOGNITION OF CONCEALED OBJECTS USING MULTIPLE ENERGY COMPUTED TOMOGRAPHY

CROSS-REFERENCE TO RELATED APPLICATIONS

This application is a continuation-in-part application of U.S. patent application Ser. No. 08/968,799 filed Nov. 17, 1997, which is incorporated herein by reference, which, in turn, is a continuation of U.S. patent application Ser. No. 08/591,839, now abandoned, filed Jan. 25, 1996, both of which applications are entitled "Apparatus and Method for Automatic Recognition of Concealed Objects Using Multiple Energy Computed Tomography". Priority is also claimed based upon Provisional patent application Ser. No. 60/006,670 filed Nov. 13, 1995.

GOVERNMENT INTEREST

The invention described herein may be manufactured, used and licensed by or for the government for governmental purposes.

BRIEF DESCRIPTION OF THE INVENTION

The present invention relates an apparatus and method for detecting concealed objects and features thereof, such as contraband in baggage, defects in articles of manufacture, or medical applications, using multiple energy computed tomography.

BACKGROUND OF THE INVENTION

Conventional X-ray scanning is used in a number of fields to detect objects or features not visible to the human eye. For example, in the medical and dental fields, X-ray systems are used to detect features of interest in rendering a clinical diagnosis, such as a fractured bone or a cavity. In the manufacturing industry, X-ray systems are used similarly to inspect parts for defects. Fractures or voids below the surface of a weld, for example, can be detected from an X-ray image, thus avoiding possible failure of the part should it be used in its defective condition. X-ray systems are also used in airports and other public facilities to inspect containers for weapons, explosives, and other contraband.

In each of the foregoing applications, the X-ray system is an imaging device without the capability of automatic identification of targets. These systems produce a gray scale image, representation of the total X-ray energy absorbed by all objects between the X-ray source and the detector. For instance, the more energy absorbed, the lighter the corresponding spot on the image. Using this projection method, the resulting images or radiographs are often difficult to interpret because objects are superimposed. Data obtained from X-ray images are generally unsuitable for automatic detection because of the complexity involved in resolving superimposed objects. A trained operator must carefully study and interpret each image to render an opinion on whether or not a target of interest is present. When an application requires a large number of radiographs to be interpreted, operator fatigue and distraction can compromise detection capability.

X-ray Computed Tomography (CT) is a technique that produces an image of a cross-sectional slice of an object from a series of attenuation measurements taken at various angles around the object. The CT image does not suffer from the super-positioning problem presented with standard radiographs. Although CT data can provide precise, quantitative information about the characteristics of objects in the scan plane suitable for automatic detection of targets, it too has limitations. Conventional CT systems take considerable time to perform a scan, to capture the data and reconstruct an image. The throughput of CT systems is low. Coupled with the size and expense of conventional CT systems, this limitation has hindered CT use in applications such as baggage or parts inspection where object throughput is a major concern.

U.S. Pat. No. 5,367,552 to Peschmann describes a method for improved CT throughput. In the Peschmann system a conventional X-ray scanner is first used to pre-scan an object, followed by CT scanning at locations selected from analysis of the pre-scan data. Although the solution taught by Peschmann provides improved detection capability over conventional X-ray systems, it has several limitations. First, it requires pre-scanning of the object with a conventional X-ray system which takes time and provides limited results as discussed above. Second, in order to save time, a CT scan is performed only at selected locations which could result in failure to identify targets of interest, especially where the target is masked or otherwise difficult to detect with a conventional X-ray scanner. Third, because the Peschmann invention uses a conventional rotating CT device, the throughput is limited by the mechanics of the rotation. Fourth, the flow of the baggage is halted at each scan location, again limiting throughput, to allow for rotation of the X-ray source around the object to acquire the data for that slice. Finally, Peschmann teaches the use of conventional single- and dual-energy techniques for generating CT data whereas a multiple-energy or multispectral technique as described herein would result in improved target identification.

U.S. Pat. No. 4,651,005 to Baba et al. describes an energy separated quantum-counting "radiography". The system described in Baba et al. provides a two-dimensional superimposed image based on the average of the energy attenuation passing through a human body. This system cannot identify unknown objects being traversed by the photon beams based on tomographic reconstruction of transmission by voxels, and does not identify objects based on reconstructed spectral transmission by voxels. The spectral content of a radiographic image generated by the Baba et al. system would be based on the average absorption of all materials between the detector and the source. As a result, when the radiograph is complex, that is when images of two or more objects are superimposed or overlap in a radiograph, those objects are not well separated in their spectral content, and have little probability of being identified by the Baba et al. system.

Therefore, there is a great and still unsatisfied need for an apparatus and method to detect and identify concealed objects and features thereof, such as contraband in baggage, defects in articles of manufacture, or medical applications, using multiple energy computed tomography.

SUMMARY OF THE INVENTION

It is an objective of the present invention to provide a new apparatus and method that enables automatic recognition of concealed objects and features thereof, with or without operator assistance. These features provide unique and distinctive measured or determinable characteristics of the objects being recognized.

It is another objective of the present invention to allow for high throughput of objects (i.e., the number of objects that can be detected per unit of time) during scanning operations without compromising detection capability.

It is yet another objective of the present invention to provide CT data using a compact stationary X-ray source array and a detector array.

It is still another objective of the present invention to provide a radiographic image and a CT image or both for operator viewing, such that the object detected is visibly contrasted relative to its environment.

It is a further objective of the present invention to provide statistically based confidence levels for target identification, and to provide a continuous learning capability for improving target identification with system use.

These and other objectives are achieved by an apparatus and method for automatic recognition of concealed objects. The apparatus uses multiple energy X-ray scanning to identify targets with a spectral response corresponding to a known response of targets of interest. Detection sensitivity for both automatic detection and manual inspection are improved through the multiple-energy, multispectral technique. The processing of detector elements in parallel is used to achieve high throughput capability. Target identification may be verified through further analysis of such attributes as shape, texture, and context of the scan data. The apparatus may use a statistical analysis to predict the confidence level of a particular target identification. A radiograph, CT image, or both may be reconstructed and displayed on a computer monitor for visual analysis by an operator. The apparatus may receive and store input from the operator for use in subsequent target identification.

Briefly, an important feature of the present invention is the combination of numerous, stationary, polychromatic x-ray sources, with linear arrays of x-ray detector elements, each element employing its own multi-channel analysis circuit, spatially configured to acquire data which can be reconstructed by computer into multi-spectral tomographic images, followed by identification of objects in the CT images from the processing of the CT images, on a voxel-by-voxel spectral basis and the characteristics of voxel grouping wherein grouping is done in three dimensional space based on prescribed level of similarity in spectral content. The present invention recognizes that the attenuation of the X-rays is a function of the X-rays' energy. The invention employs this characteristic in an unique fashion to provide greater detection capability over that of more conventional X-ray apparatus. For example, by using multiple energy spectra, the object attenuation behavioral curve can be derived and compared to attenuation behavioral curves of known objects, frequently enabling a precise and accurate identification of the objected being detected.

The present invention separates superimposed objects through the process of CT. When a voxel in the CT image lies entirely within an object, the voxel spectral content will be indicative of the object's spectral absorption characteristics. The present invention enables the identification of unknown objects using the voxel's spectral content and its relationship to similar neighboring voxels as determining factors.

BRIEF DESCRIPTION OF THE DRAWINGS

FIG. 2 is a perspective view of the automatic recognition system of FIG. 1, illustrated in use in conjunction with a baggage inspection station according to one embodiment of the present invention;

Similar numerals refer to similar elements in the drawings. It should be understood that the sizes of the different components in the figures may not be in exact proportion, and are shown for visual clarity and for the purpose of explanation.

DETAILED DESCRIPTION OF THE INVENTION

Figure 1:
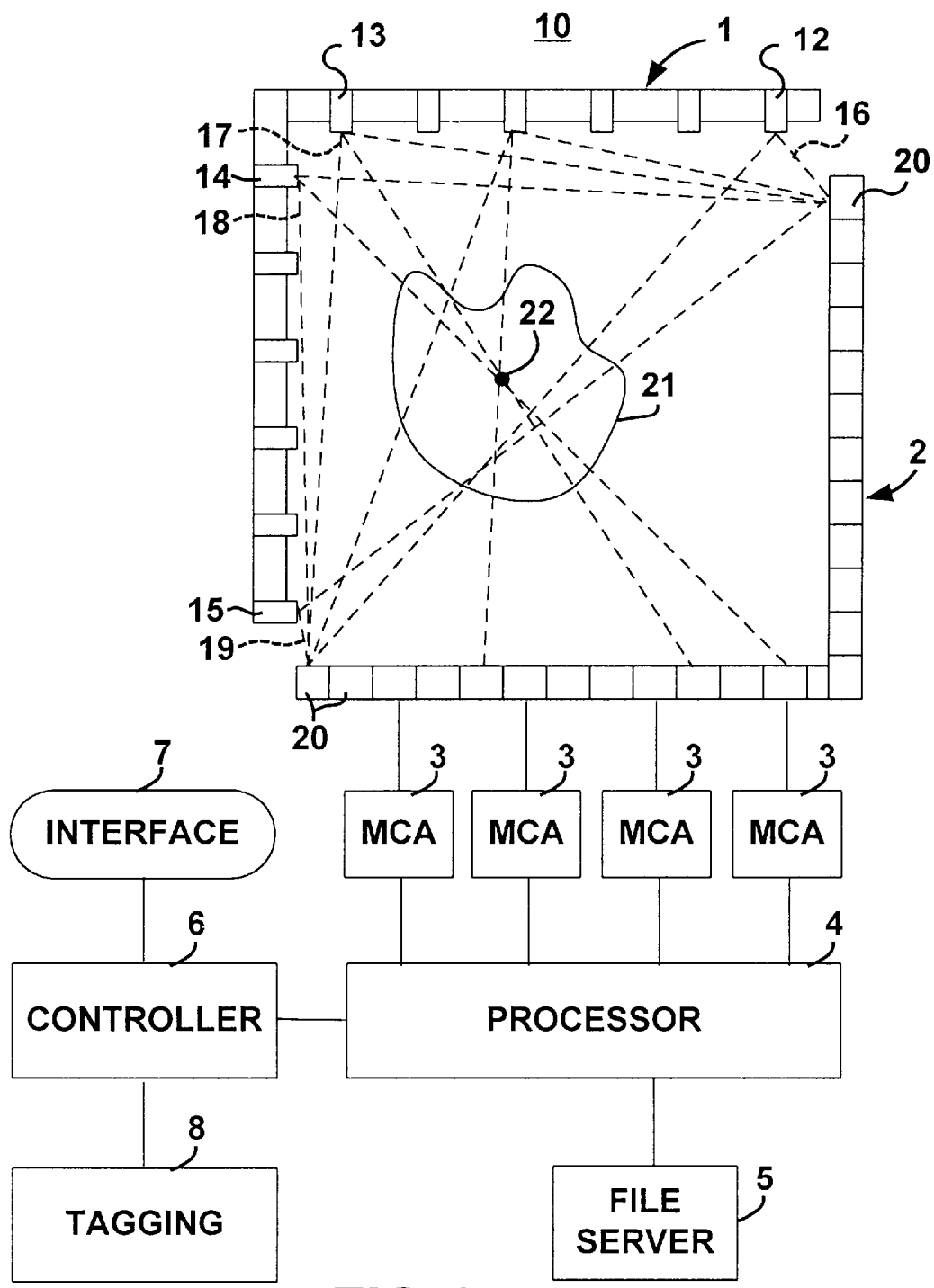
FIG. 1 is a high level schematic diagram of an automatic recognition system according to the present invention.

FIG. 1 illustrates an automatic recognition system 10 according to the present invention. By way of overview, the system 10 is first described by reference to its major components. The system 10 generally includes a source array 1 and a detector array 2. The source array 1 in this particular embodiment is L-shaped and is comprised of a plurality of X-ray sources, i.e., 12–15 that are spaced apart along the length of the source array 1, and that provide a series of co-planar fan beams 16–19, in response to a signal from a controller 6. Each fan beam 16–19 is comprised of X-ray photons having known energy distribution of varying energy levels within a fixed energy band. Source array 1 is positioned opposite to and separated from the detector array 2 to form a space within which object 21 can be scanned.

Detector array 2 includes a plurality of detector elements 20 that are co-planar with the X-ray sources 12–15 so that the fan beams 16–19 from the sources 12–15 are captured by the detector elements 20. According to another embodiment, the source array 1 may include a plurality of successive source elements that are disposed in distinct planes, and the detector array 2 may include a plurality of successive detector elements that are disposed co-planar with corresponding source elements. Though the invention is described herein in connection with X-ray sources and detectors, it should be clear that any suitable ionizing radiation sources and detectors of ionizing radiation can be used. Examples of suitable detectors include cadmium zinc telluride, cadmium telluride, mercury iodide, thallium bromide, various silicon based detectors, etc.

Detector array 2 is also L-shaped, and the detector elements 20 are arranged at known intervals along its length. If unimpeded, photons traverse along straight lines between the individual photon sources in array 1 to the individual detector elements in array 2. The detector element 20 absorbs those photons encountered and thereafter provides a pulse of electrons to a corresponding multi-channel analyzer (MCA) circuit 3. The number of electrons in the pulse is proportional to the energy level of the photon absorbed by the detector element 20. The path the photon is considered to be the straight line between the emitting source and the absorbing detector element.

An MCA 3 is provided for rapid processing of the voltage signals from detector elements 20. Though only four MCA's are illustrated, a preferred embodiment of the system 10 dedicates a separate MCA to each individual detector element 20. The output of each MCA 3 is a count per energy band of the number of photons absorbed by one detector element 20 connected (or corresponding) to the MCA 3, over a given period of time. Reference is made to the Baba et al. U.S. Pat. No. 4,651,005 (or U.S. Pat. No. 4,794,257) described above, which is incorporated herein by reference, and which describes the use of an MCA in performing analyses for medical purposes.

Processor 4 is preferably a computer processor with parallel processing capability. Processor 4 uses CT reconstruction algorithms to reconstruct and analyze, from the number of photons counted by the MCA's 3, a tomographic image of the cross-sectional slice of object 21 which was scanned to acquire the data. A pixel in a tomographic image of a cross-sectional slice is called a voxel because it represents material in a volume element whose dimensions are those of the pixel and the thickness of the slice. The photon counts from the MCA's 3 are also used to construct a projection radiographic image to provide a familiar visual image for display on an interface 7. A review of CT reconstruction techniques, convolution, artifacts, the effect of beam width, etc. is described in "Standard Guide for Computed Tomography (CT) Imaging," ASTM, Designation E 1441-93, April 1993, which is incorporated herein by reference.

Each MCA 3 counts the number of photons for a set period of time in each energy level or band within the selected energy spectrum. In this particular example five energy bands $E_1$, $E_2$, $E_3$, $E_4$, and $E_5$ are selected for illustration purpose only. If the number of photons to be counted was unlimited and time for counting was unlimited, the accuracy of the method described herein would improve with the number of bands. Generally that is not the case and so an optimal number of bands does exist. Determination of the optimal number of bands is outside of the scope of this patent. A good discussion can be found in U.S. Pat. No. 4,794,257. The count of photons in each of these energy bands when the object 21 is not present is indicative of the energy spectrum of the source, e.g. 12. The photon count the MCA 3 associates with each detector element 20 in the detector array 2 at each of the energy levels $E_1$, $E_2$, $E_3$, $E_4$, and $E_5$ will be depend on what the object 21 is.

The intensity I(x) is determined by the following radiometric equations:

$$dI(x) = -I(x)n\sigma dx,$$

$$I(x) = I_0 \cdot e^{-n\sigma x},$$

$$n = N\rho/A, \text{ and}$$

$$n\sigma = \mu,$$

where x is the distance traveled by the photon through the object 21, n is the number of atoms per cubic centimeter, $\sigma$ is the probability per atom for scattering or absorption of atoms, N is the Avogadro number, A is the atomic mass of the material, $\rho$ is the density of the material, and $\mu$ is the linear attenuation coefficient of the material being identified.

Processor 4 determines and analyzes the attenuation factor $\mu$ as defined by the following equation:

$$\mu_n = (1/x)\ln(I_{0n}/I_n),$$

where $I_{0n}$ is the intensity of the incident beam from a source, e.g. 12, within energy band $E_n$, and $I_n$ is the intensity of the exit beam incident on the detector element 20 within energy band $E_n$ after passing through object 21.

The photon count in each energy band is processed independently so that processor 4 provides several, in this example, 5 attenuation factors $\mu_1$, $\mu_2$, $\mu_3$, $\mu_4$, and $\mu_5$, corresponding to the energy bands $E_1$, $E_2$, $E_3$, $E_4$, and $E_5$, respectively. These five attenuation factors provide significant data related to the content of each voxel within the object 21. In another embodiment, the number of energy bands is increased so as to optimize the data obtained about the voxel content. While the present invention is described in connection with five energy levels for illustration purpose only, it should be clear that a different number of energy bands can be used, and that a greater number of energy would be desirable in certain applications.

Figure 8:
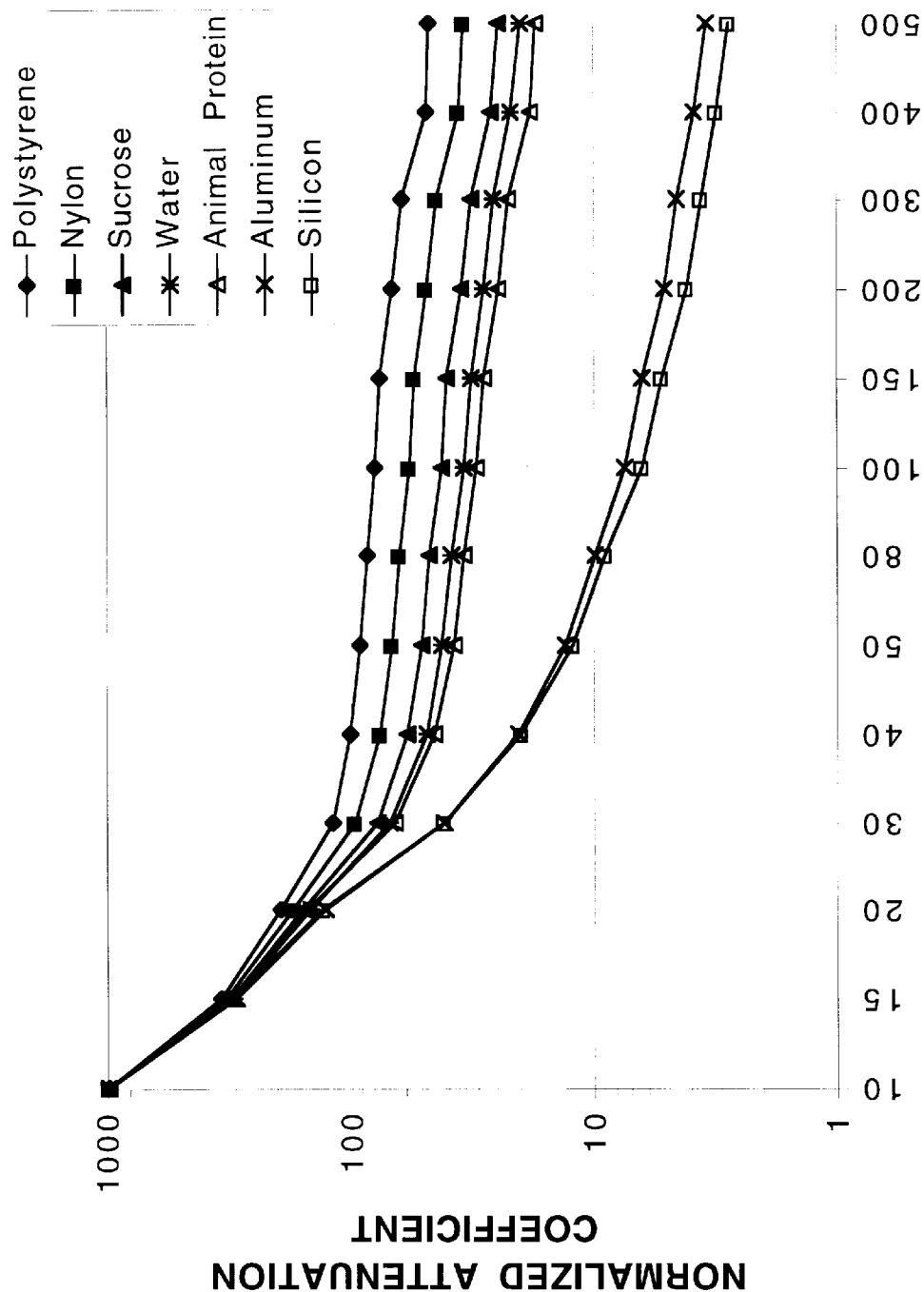
FIG. 8 is a plot of multiple bar charts of the X-ray attenuation coefficients for selected materials at various photon energies, wherein each bar chart is scaled such that the attenuation coefficient at 10 KeV is the same value. The result illustrates that shape of the curves and not simply the relative area under the curves differs and can be used to characterize the corresponding materials.

Once the attenuation factors $\mu_1$, $\mu_2$, $\mu_3$, $\mu_4$, and $\mu_5$ are determined, they are matched against attenuation levels for known materials. Reference is made to FIG. 8. This allows the processor 4 and/or the user to identify the object 21 from its X-ray attenuation factors.

Tagging system 8 is provided in this particular embodiment for applying an identification tag to object 21 in response to a signal from controller 6 when a positive target identification is made by the apparatus. A defective part or baggage that contains contraband is thus tagged for subsequent human attention. In an alternative embodiment, an automatic sorting and materials handling system may be used to automatically separate defective parts from nondefective parts.

User interface 7 is provided to display enhanced X-ray and CT image data for human viewing and to receive input from a human operator. Interface 7 is electrically coupled to controller 6 for sending and receiving data. Interface 7 also is used to download selected images from file server 5 for display to the human operator. X-ray and CT images may be enhanced by, for example, using a unique color for targets of interest. In a preferred embodiment, interface 7 is a large, high-resolution color touchscreen for ease of viewing and input operation. The interface 7 can also be used to facilitate the self-learning capability of the system 10.

Figure 2A:
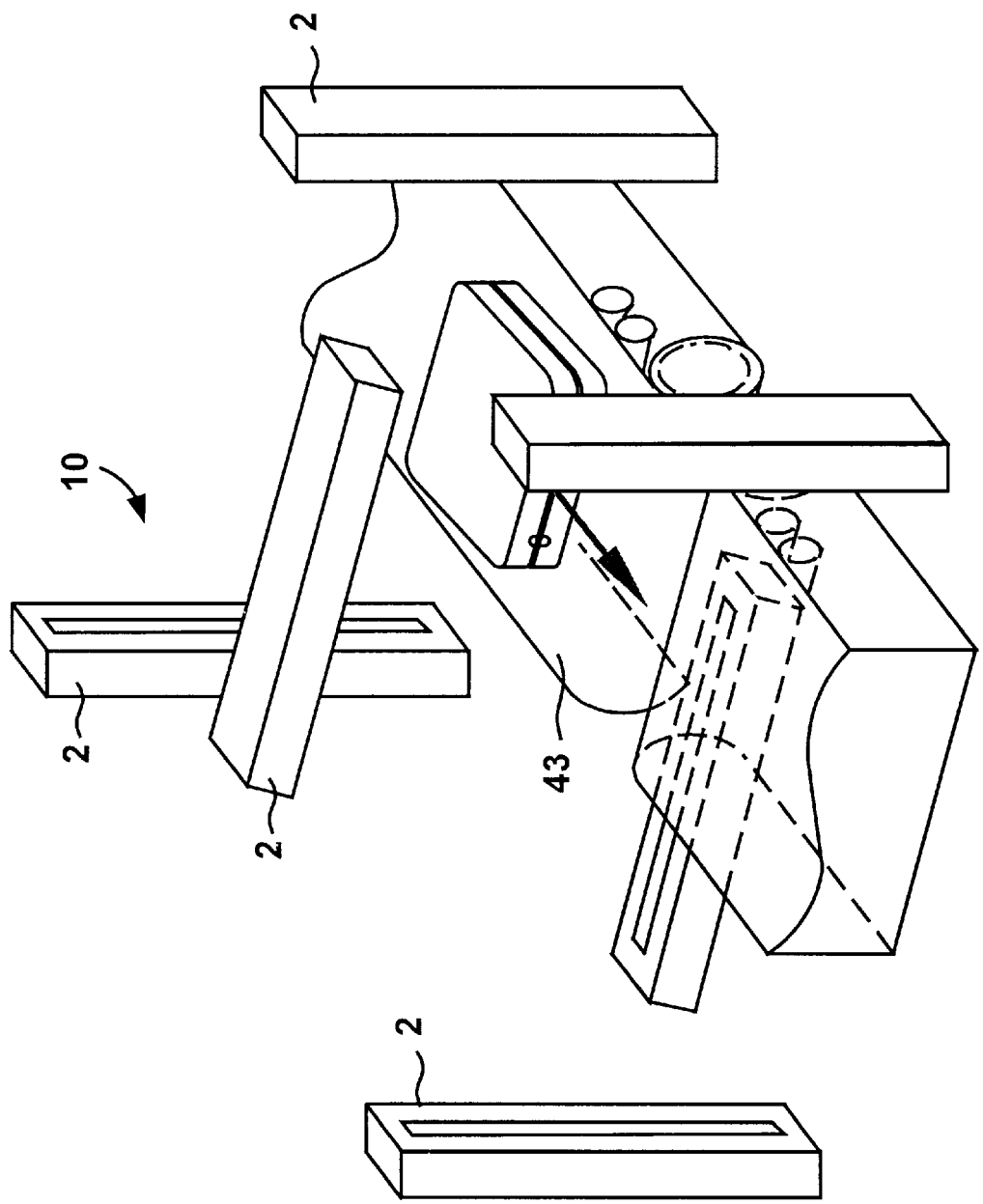
FIG. 2A is a perspective view of an automatic recognition system according to another embodiment of the present invention, illustrated in use in conjunction with a baggage inspection station.

With reference to FIGS. 2 and 2A, a conveyor belt 43 or another suitable means is provided to move object 21 forward through the space defined by source array 1 and detector array 2 for scanning. As object 21 is moved forward, each of the X-ray sources 12–15 is activated in a predetermined sequence by controller 6 such that only one X-ray beam 16–19 is produced at any one instant by one source array 1 and its corresponding co-planar detector array 2. It should be clear that two or more source arrays 1 and their corresponding detector arrays 2 can be activated simultaneously, provided the scanning function from one system 10 does not interfere with the scanning operation of the another system 10. For example, the simultaneously activated systems 10 are not co-planar and the source beams are collimated to prevent photons emitted in one plane from entering the detector in another plane.

The path of a particular photon that caused a pulse of electrons to be emitted from a detector element 20 can thus be determined from the known position of source 12–15 from which it was emitted and the known position of the detector element 20.

By way of example, X-ray source 12 is activated first, emitting photons of known spectral content (e.g. the number of photons in each of the defined five spectral bands) to form a fan beam 16, part of which passes through site 22 in object 21. As each photon is absorbed by a detector element 20, a pulse of electrons proportional to the energy level of the photon is inputted to the corresponding MCA 3. This MCA 3 outputs the count of photons in each of the five energy bands (i.e., spectral photon count), detected by the particular detector element 20 within a given time frame. Though the MCA 3 is selected here for illustration purpose, it should be clear that other appropriate methods and devices can be used to provide the spectral photon count.

Figure 9:
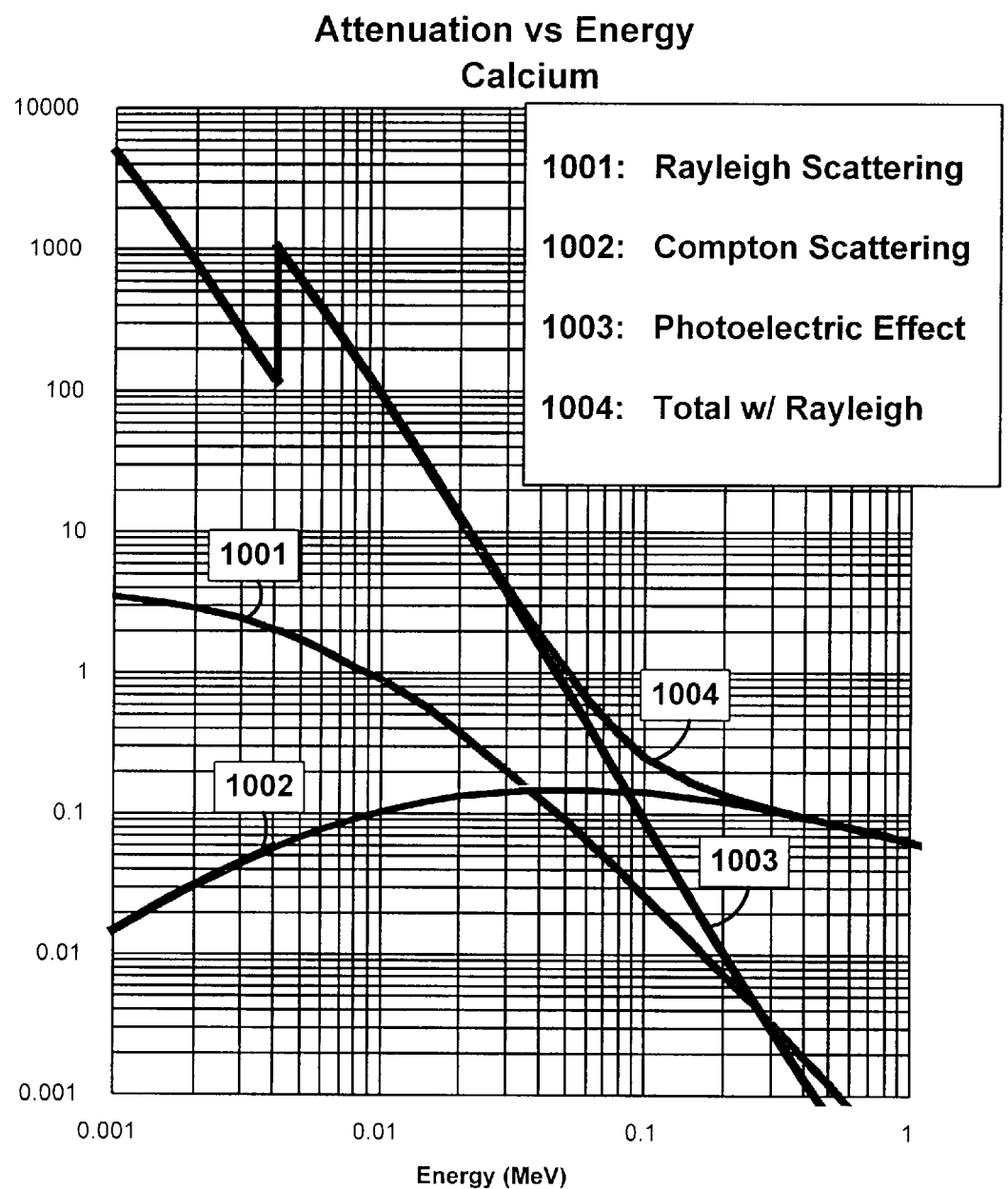
FIG. 9 is a plot of the attenuation coefficient versus energy for calcium.

A beam of x-rays exhibits a characteristic exponential absorption in its passage through matter. Three predominant types of interaction occur, each with different dependence on the photon energy: photoelectric effect, scattering, and pair production. Absorption form the photoelectric effect predominates at lower energies and exhibits characteristics discontinuities as seen in FIG. 9. The discontinuities occur at the binding energies of the electrons in the atom. For lighter elements pair production is of little significance and for all elements pair production only occurs above 1.02 MeV. This leaves Raleigh scattering and Compton scattering as the only other significant contribution at energies generally of interest. FIG. 9 illustrates that the total attenuation is a fairly complex function of energy. The dependence of attenuation on energy is unique for every element. It is well known that the mass attenuation of a mixture or of a compound is the sum of mass attenuation of the individual elements weighted in proportion to their relative abundance. The result is that the mass attenuation coefficient of different materials can be used to characterize those materials. The difference in the mass coefficient will depend on how different the relative abundance of the individual elements in the material is. Another words, it is possible to have dissimilar materials which have the same mass coefficient.

The linear attenuation coefficient is the mass coefficient times the density of the material and is the property which can be calculated from the MCA data. Therefore materials of the same relative abundance of elements can still result in a different linear attenuation coefficient.

FIG. 8 is a set of bar charts of the X-ray attenuation coefficients for selected materials at various photon energies, wherein each bar chart is scaled such that the attenuation coefficient at 10 KeV has the same value. The scaling of the attenuation coefficients removes the effect of material density, which is not energy dependent, from the coefficients. The relationship between the scaled coefficients for one material are characteristic of the energy dependence of that material's x-ray attenuation. Hence, we have separated the energy dependence from the density dependence. Both can now be used to characterize the material in the voxel. It should be noted that with greater energy resolution, i.e., more data points in the curve, the probability that the attenuation curves will be unique from material to material increases.

The use of a MCA 3 for each detector element 20 increases the processing speed of the system 10, so as to limit the amount of time needed to activate source 12 and to collect the resulting attenuation data. In this way, object 21 may be moved continuously through the apparatus during scanning operations while still providing sufficient data for automatic target identification. The MCA's 3 also provide for field adjustment of the selected energy ranges.

Figure 10:
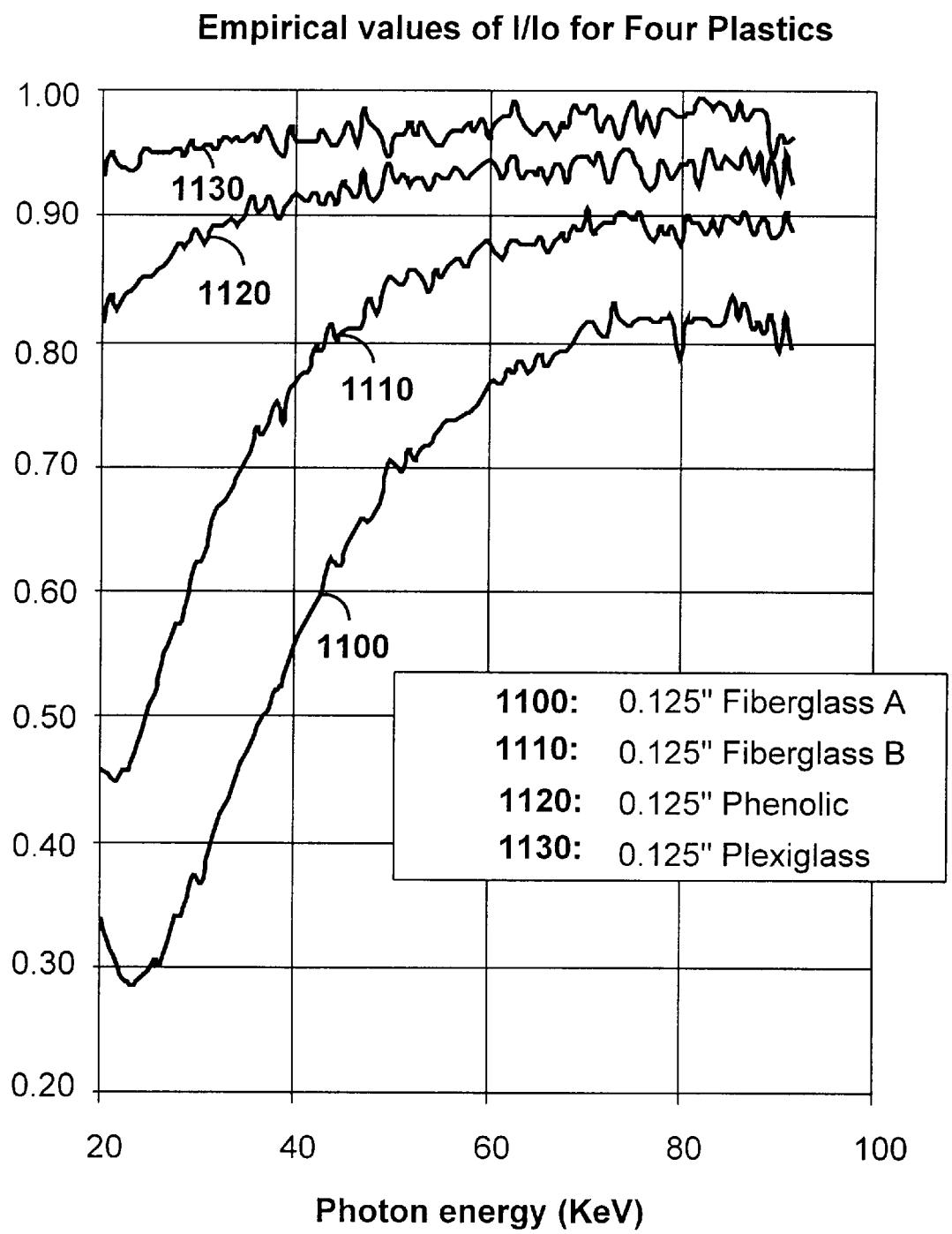
FIG. 10 is a plot of the ratio of $I/I_0$ for four different plastic materials calculated from measured data.

As the fan beam 16 passes through object 21, some of the photons of beam 16 are absorbed by the material at site 22 within object 21, some photons pass through unaffected, and some photons are scattered showing up as lower energy photons. In that the path of scattered photons is unknown, they are a source of noise. A collimator placed in front of detector element 20 decreases the portion of scattered photons impinging upon the detector element 20. In general, the number of photons of any energy range impinging on detector element 20 will be less after passing through the material of object 21 than would have been if no material were present. In as much as the proportional decrease in number of photons of different energy is a unique function of the chemical composition of the material, the ratio of I/Io can be used to characterize the material. For example, FIG. 10 is a plot of the ratio of I/Io for four different plastic materials calculated from measured data.

The attenuation coefficient, $\mu$, as a function of photon energy can be used to characterize the material of object 21. By using sources 12–15 having a continuum of energy, and capturing the resulting multi-energy spectrum after the photons have traveled through object 21, and comparing that passing through material at site 22 to that which would be captured with no material present at site 22, more data are provided about the chemical composition of object 21 over systems that use only single- or dual-energy technique. Used in conjunction with other image processing means, such as described below, this multispectral data provides far greater discernment of contraband in baggage, defects in articles of manufacture, and similar applications.

Processor 4 performs the reconstruction of the object 21. Attenuation of the X-rays by the material at site 22 is contained in the data acquired from those detector elements which acquired X-rays passing through site 22. Tomographic reconstruction of the voxel at site 22 is performed by appropriate mathematical combination of the data. For the geometric configuration of the X-ray source and X-ray detector of FIG. 1 the Algebraic Reconstruction Technique (ART) is appropriate for calculating the tomographic image. For other geometries other reconstruction techniques can be used.

The ART can be used in the system 10 to produce tomographic images from a limited number of projections (i.e., scans) with limited coverage. This is particularly useful in applications where space constraints are important and thus limit the number of projections and the angles at which projections can be made. Such applications are amenable to solution by algebraic techniques; imaging equipment can be designed to fit within space constraints, while still providing the required identification sensitivity.

A simplified object is reconstructed using the ART algorithm to illustrate convergence of the algorithm. Reference is made to Andersen, Anders H., "Algebraic Reconstruction in CT from Limited Views", IEEE Transactions on medical Imaging, Volume 8, No. 1, pages 50–55, March 1989; and Swindell, W., and Barrett, Harrison H., "Computerized Tomography: Taking Sectional X Rays", Physics Today, December 1977, pages 32–41, December 1977, which are incorporated herein by reference. Reference is also made to N. J. Dusaussoy et al., "The Extended MENT Algorithm: A Promising Reconstruction Algorithm for Computerized Tomography," IEEE, 1989, pages 1460–1463, which is incorporated herein by reference, and which provides a discussion on performing CT reconstruction from limited data using a priori information.

Other forms of algebraic reconstruction, such as Simultaneous Iterative Reconstructive Technique (SIRT) and Iterative Least-Squares Technique (ILST) would produce similar results and could be used in the alternative with the present invention. ILST and SIRT, like ART, are based upon an iterative approach in which the measured projection data are related to a discrete distribution of the absorption coefficients through a set of linear simultaneous equations. The algorithms differ in the way correction terms are calculated and reapplied to subsequent iterations. The advantages and limitations of the various algorithms are well known in the art of computerized tomography.

Figure 1A:
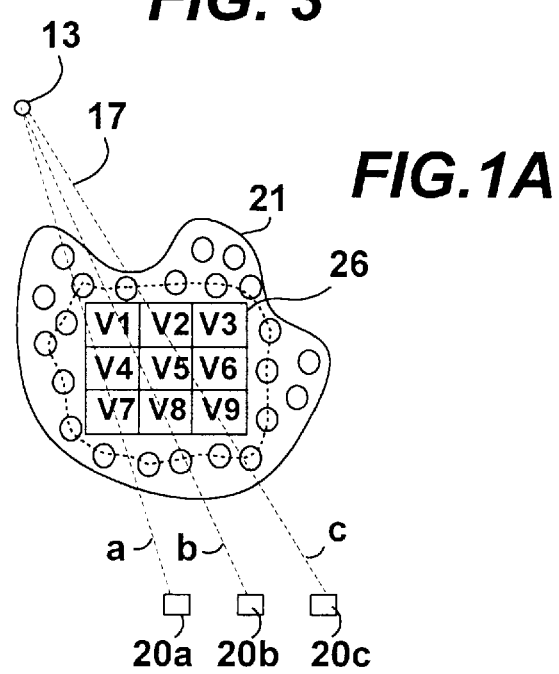
FIG. 1A is a representation of an object or part thereof, illustrating an exemplary (exaggerated) voxel arrangement recognized by the system of FIG. 1.

As illustrated in FIGS. 1 and 1A, five projections fan beams 16–19 are taken through object 21 containing nine voxels V1–V9 of interest. Each voxel is homogeneous with an attenuation value shown below in Table 1 below. The fan beams 16–19 pass through two or more voxels V1–V9, and are projected onto detector array 2, where the intensity I of the fan beam is measured. As shown, the sources for the fan beams are housed in an L-shaped source array 1, and the detectors for acquiring projection data are similarly housed in a separate L-shaped detector array 2. Even though this configuration can result in a limited number of fan beams with limited coverage, the reconstruction of a tomographic image is possible, as illustrated below. In an alternative embodiment, a U shaped source and a U shaped detector array are used to increase projection coverage of the object.

Turning to Table 1 below, the actual attenuation values of the nine voxels are shown. Recall that:

$\mu = \ln(I_0/I)$ when $x=1$.

For illustration all the voxels will be considered to have a thickness, $x$, of value 1. For a photon beam passing through multiple voxels, each of the same dimension and each characterized by a attenuation coefficient, the effective attenuation coefficient along the beam path is the sum of the individual coefficients:

$\mu \rho = \mu_1 + \mu_2 + \ldots$

Given these attenuation values, the measured values from the fan beams 16–19 are determined as the sum of the attenuation values of the voxels through which the fan beams pass. The projection value, $\mu \rho$, is similarly obtained by summing $\mu$ along each row and column. The projection data that would be measured from projections 120–123 are thus readily determined in this illustration by summing the appropriate elements of the known object.

TABLE 1

| Actual Object Values | | |
|---|---|---|
| 1 | 2 | 3 |
| 8 | 9 | 4 |
| 7 | 6 | 5 |

The first step in this example is to use the data from one fan beam to produce an initial estimate of object 21 as shown in Table 2. This is done by dividing the measured projection values evenly over the elements through which the projection passes. For example, the measured value of 6 for the top ray of projection 123 is even distributed over the three cells through which the projection ray passed, resulting in three equal cell values of 2. Similarly, the measured values 21 and 18 are divided evenly among the three cells corresponding to their respective projections. A first estimate of the reconstructed image of object 21 is thus formed.

TABLE 2

| First-Iteration Reconstruction | | |
|---|---|---|
| 6→ 2 | 2 | 2 |
| 21→ 7 | 7 | 7 |
| 18→ 6 | 6 | 6 |
| ↓ | ↓ | ↓ |
| (15) | (15) | (15) |

The next step is to calculate correction values to be applied to the estimated values of Table 2. This is done by comparing the first-iteration reconstruction, which was made from data obtain from projection 123, with one of the other four projections. Here, the vertical elements of Table 2 are summed, as shown above in parentheses, and compared with the measured values from vertical projection 121. In this first iteration, all three columns result in an estimated projected value of 15 while the measured values are 16, 17, and 14, respectively. A second-iteration estimate of object 21 is then formed, as shown in Table 3, by distributing the difference between estimated and measured projection values equally among the projected cells. By way of example, the estimated projection value for the first column of Table 2 is 15 while the actual measured projection value was 16. A correction of plus one is thus distributed over three elements, resulting in a cell correction of plus one-third for this particular ray projection.

TABLE 3

| Second-Iteration Reconstruction | | | |
|---|---|---|---|
| $2^{1/3}$ | $2^{2/3}$ | 1 | |
| $7^{1/3}$ | $7^{2/3}$ | 6 | |
| $6^{1/3}$ | $6^{2/3}$ | 5 | $(8^{2/3})$ |
| | (14) | (15) | |

The third iteration reconstruction is made using measured values from diagonal projection 122 in comparison with the estimated values shown in parentheses next to Table 3. As before, correction values are evenly distributed among the projected cells resulting in the values shown in Table 4. By way of example, the estimated projection value of $8^{2/3}$ is $2^{2/3}$ more than the measured value of 6. As the diagonal ray of projection 122 passes through just two cells of object 21, the error is divided evenly among the corresponding two cells of Table 4, resulting in a correction of plus $1^{1/3}$.

TABLE 4

| Third-Iteration Reconstruction | | | |
|---|---|---|---|
| | $2^{1/3}$ | $1^{1/3}$ | 1 |
| | $7^{1/3}$ | $7^{2/3}$ | $4^{2/3}$ |
| $(8^{2/3})$ | $6^{1/3}$ | $6^{2/3}$ | 5 |
| (15) | $(11^{1/3})$ | | |

The fourth iteration reconstruction is similarly produced using measured values from diagonal projection 120 with the corresponding estimates from the previous iteration.

TABLE 5

Fourth-Iteration Reconstruction

| | | |
|---|---|---|
| $2^{1/3}$ | 2 | $2^{1/3}$ |
| 8 | 9 | 4 |
| $7^{2/3}$ | 6 | 5 |

As the actual values of object 20 are known in this example, the root-mean-square (rms) error for each of the above iterations can be calculated. The rms errors of iterations one through four are 1.4, 1.2, 0.7, and 0.5, respectively. This monotonously decreasing error illustrates the convergence of the ART algorithm with limited projection data and limited coverage. Methods to apply this and similar algebraic reconstructive algorithms to the data obtained with the present invention apparatus are well known in the art. See, for example, A. Andersen, Algebraic Reconstruction in CT from Limited Views, IEEE Transactions on Medical Imaging, Vol. 8, No. 1, March 1989, which is incorporated herein by reference.

Since the differing spectral data ($\mu(E_1), \mu(E_2), \ldots$) were acquired by the same detector elements 20, for the same voxel, at the same time, the voxels in the respective spectrally differing tomographic images are also coincident, thus causing inherent spatial fusion of the data. This significantly simplifies the data fusion process. The set of values for the five energy bands for any one voxel site is endemic of the actual spectral attenuation occurring at that voxel and can be used for characterizing the material at the voxel site.

With reference to FIG. 1A, object 21 is shown, for illustration purpose only, to contain another object 26 to be identified. Object 26 includes 9 voxels V1–V9. Source 13 emits an X-ray fan beam 17, which, if unimpeded, would strike a detector element 20a. Each of the detector elements 20a, 20b, 20c, etc. and its associated MCA's 3, count the number of photons in each of the preset energy bands $E_1$, $E_2$, $E_3$, $E_4$, $E_5$, etc. The resulting values would be endemic of the source spectrum, and is a function of the intensity $I_0$ as determined by the above radiometric equations.

Ray a of the fan beam 17 passes through voxels V1, V4, V7. In each of these voxels a number of photons are absorbed. The number of photons that are not absorbed will be measured by the detector element 20a. For each energy band $E_1$, $E_2$, $E_3$, $E_4$, $E_5$, etc. the intensity of the spectrum $I(E_1)$ can be expressed by the following equation:

$$I(E_1)=I_0(E_1)\cdot\exp[-(\mu_1(E_1)\cdot X_1+\mu_4(E_1)\cdot X_4+\mu_7(E_1)\cdot X_7)],$$

where $X_n$ is the distance through which ray a travels through voxel n (in this example, n=1, 4, 7), and $\mu_n$ is the linear absorption coefficient for voxel n. $I_0(E_1)$ represents the number of photons of energy $E_1$ when object 21 is not present. $I(E_1)$ represents the number of photons of energy $E_1$ when object 21 is present.

The CT calculates $\mu(E_1)$ for each voxel. Each voxel, such as voxel V1, can be characterized by a set of $\mu$ values, for example: $\mu_1(E_1), \mu_1(E_4)$ and $\mu_1(E_7)$.

For object 21 in continuous motion while attenuation data are acquired by detector elements 20, the scan is helical and the tomographic reconstruction is a type of helical tomographic reconstruction.

Processor 4, after calculating the $\mu$ values, stores these values in file server 5 for later reference. Processor 4 then performs a matched filtering process whereby it fits the spectral attenuation coefficient ($\mu$) values of each voxel to that of various known target values also stored in file server 5 (FIG. 8). Matched filtering determines the probability which the voxels' $\mu$ values have of matching those of known materials. For example, processor 4 determines the probabilities that the material is aluminum, Teflon, water, etc., and stores that result in the file server 5. From the comparison based on the calculated probabilities, a coded image is constructed which exemplifies voxel-by-voxel the most probable materials and the degree of probability. For some cases, the effect of certain artifacts in the reconstructed image can be reduced by calculating a new set of images from the difference in the values of the respective voxels in the respective spectral images. In that case the difference images are fit to target values instead of the spectral images themselves to construct a coded image which exemplifies voxel-by-voxel the most probable materials and the degree of probability. A matched filtering process of potential use in the present invention is described in R. M. Wallingford, et al., "Application of Two-Dimensional Matched Filters to X-Ray Radiographic Flaw Detection and Enhancement", Revs of Prog. in QNDE, Vol. 11, 1992, pages 879–886, which is incorporated herein by reference.

Processor 4 then performs a linking process whereby it analyses the coded images by looking for groupings of neighboring voxels whose composition is similar or nearly similar. Processor 4 compares the grouping size and shape to that of the probable material to further uniquely identify the object. Processor 4 may be used to perform other analyses to measure or calculate unique parameters which are known to increase the probability of recognizing objects. The data can be Fourier transformed and a spatial frequency characterization made. The data can be wavelet transformed to enhance finding object shapes. Characteristics such as 3-dimensional roundness, granularity or texture can be determined by Fractal analysis. These and other data processing techniques are well known in the art and may be practiced with the present invention for certain applications. The final result of this data analysis can be either a decision on whether a particular feature was detected, or can be an enhanced image for human viewing, or both.

A determination for the user is the proximity or maximum distance between neighboring voxels which can be linked (or grouped). This criteria for grouping voxels is obtained empirically through experience. A group probability which is the average of the matched probabilities for all the voxels in the group can be calculated. The group probability of the resultant grouped voxels is compared to those of selected materials. The linking process results in added data, and as a result further increases probability of correct identification of object 21. The linking data, along with data previously described but calculated for the individual voxels in the group, is fed into a neural network system for final identification of the grouped voxels. Linking processes of potential use in the present invention are described in M. S. Chackalackal et al., "NDE X-Ray Image Analysis Using Mathematical Morphology", Rev. of Prog. in QNDE, Vol. 9, 1990, pages 721–728; and M. S. Chackalackal et al., "NDE X-Ray Image Analysis Using Mathematical Morphology", Rev. of Prog. in QNDE, Vol. 9, 1990, pages 887–894, both of which are incorporated herein by reference.

Variation in measured energy response between detector elements occurs naturally due to random electronic and material differences in the elements. Variation occurs in the total beam intensity from x-ray source spot to source spot due to random differences in the construction of the individual source spots. Fixed variation in measured beam intensity at the detectors occurs due to the different entry angles of the x-ray beam into the detector elements. The x-ray beam intensity varies with its take-off angle from the x-ray source spot. Beam intensity decreases as the square of the distance between from the x-ray source spot to the detector elements and can vary considerably. Variation in beam intensity occurs over time due to aging of detector and source components. The present invention includes methods and calibration for correction for these variations.

$I_0$ is measured every few seconds by controller 6 and stored for every source detector combination. The current value of $I_0$ for each source—detector combination is that which is used in the calculation of the ratio $I_0/I$. This naturally corrects all variations which occur in $I_0$. Gain and offset corrections are calculated for each input channel during initialization of the system and used to correct energy response variation between detector elements. The gain and offset corrections for each input channel are fed to the electronic operational amplifiers which are part of the MCA 3. Methods of calculating and implementing gain and offset corrections are well known to the electronic industry. Hence composition and temporal variation in source and detector elements are corrected.

The algebraic reconstruction technique (ART) employs a weighting matrix which is a function of the relative positions of the sources and detectors in the calculation of the reconstructed voxels. In the present invention the weight matrix values are calculated based on the actual geometric relationship between each x-ray source spot and each detector element, thereby correcting geometric differences. The method of calculation is well described in the references.

Tagging system 8 is used in one embodiment to automatically tag a container or part when a positive identification is made. An alternative embodiment could include an automatic sorting and material handling system in place of tagging system 8. User interface 7 is used to both display the results for human viewing and to receive input from the operator. Initial calibration of the system can be achieved using interface 7 to input the correct response for scan objects of known content. The same feature can be used for continuous improvement of the system.

Continuous improvement is performed by a self-learning method provided for in the system. Objects 21 of known material and identification are scanned by the system. The system in performing its feature discerning operations will find voxels of like material, group the voxels into shapes, calculate parameters characterizing shape, size, and texture even though the new object does not correlate to any known object. The operator identifies the calculated grouped parameters and instructs the system 10 to add the new set of parameters to its list of known objects, and provides an identifier (i.e., a name) for the new object. The system 10 now includes the new object in its matching for automatic detection.

When the system 10 is first used, it will have little knowledge about the concealed objects to be identified and recognized. As these objects are found by the system 10 or by the user, the information acquired by the system 10 will be correlated with the correct object identification and characteristics. The system 10 will display a radiographic image of the object and of each selected tomographic slices in the object. The operator positions a cursor on the image area where an item is found and enter its description through a keyboard or menu. The system software forms the relationship between the X-ray data acquired or calculated for that location and the operator entered description. This relationship is stored such that the next time a similar object is seen by the system 10, the system 10 will make the same identification. The operator will confirm the identification and feed back whether the system 10 was correct or wrong. The system 10 will respond by increasing or decreasing its certainty of the relationship. With sufficient positive reinforcement of a relationship, the certainty parameter will exceed some chosen threshold and by definition the system 10 will then have learned the object being identified. This process is continuous. The certainty parameter may fluctuate based on the confirmation result.

FIG. 2 is a schematic representation of one embodiment of the invention developed to meet the specific needs of a particular baggage inspection application. In this application, baggage throughput as well as system cost and size are major concerns. The system must function at normal baggage handling rates (up to 2 feet per second), fit in a limited space, and must be compatible with existing baggage handling equipment. This is accomplished with the system 10 illustrated in FIG. 2. An X-ray source array 1 and a photon energy absorbing detector array 2 are arranged in a vertical plane between the ends of two conveyor belts such that a bag moving from one conveyor belt 43 to another will come between the X-ray source array 1 and detector array 41. The spacing of sources and detectors provide multiple beam paths, which allow for computed tomography with no moving parts within the apparatus. Although other arrangements can be used, the square geometry of the source and detector arrays provides sufficient room for baggage to pass through, while minimizing space requirements for the apparatus. Linear and relatively short components allow for a modular design that can be adapted to various geometries. The arrays 1 and 2 can be, but do not need to be, located at a gap in the conveyor system to reduce signal interference from the conveyor hardware. The system may be designed such that it can be scaled geometrically in size and resolution while still employing the same mathematical analysis and using the same basic components. In this way, systems can be easily customized for a particular application without a huge design effort.

Figure 3:
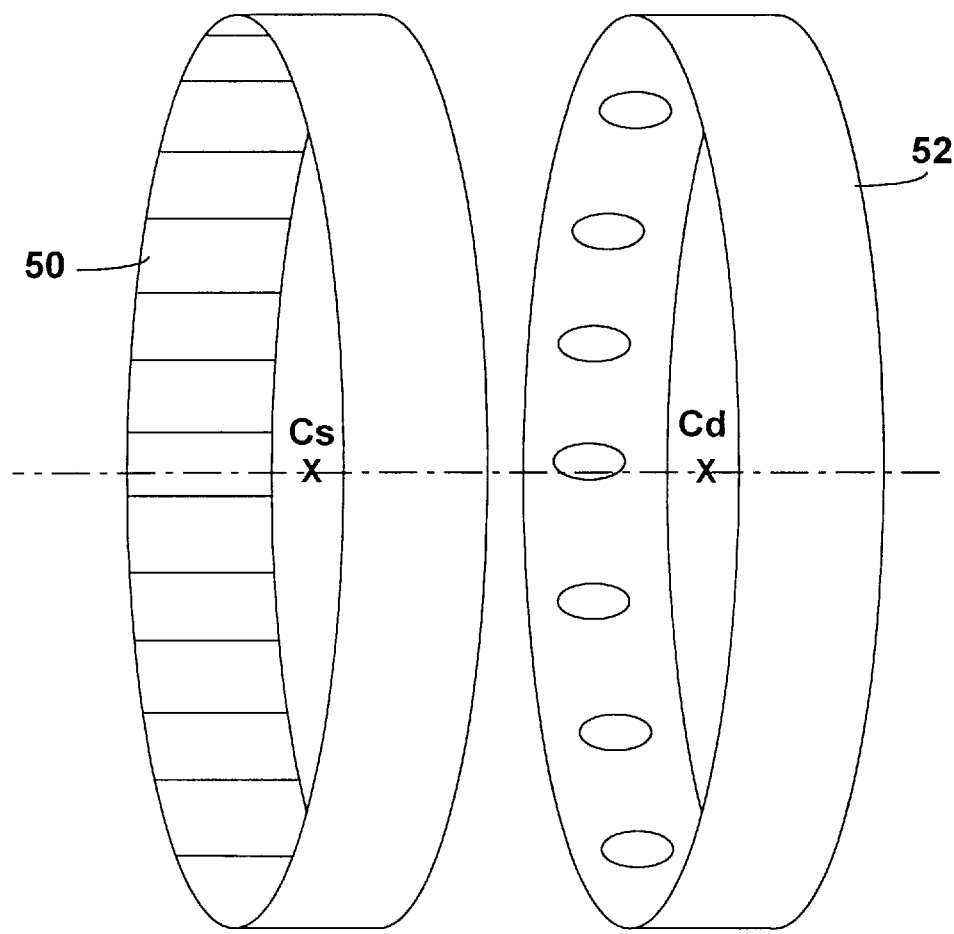
FIG. 3 is a schematic representation of another embodiment of the automatic recognition system according to the present invention.
Figure 3A:
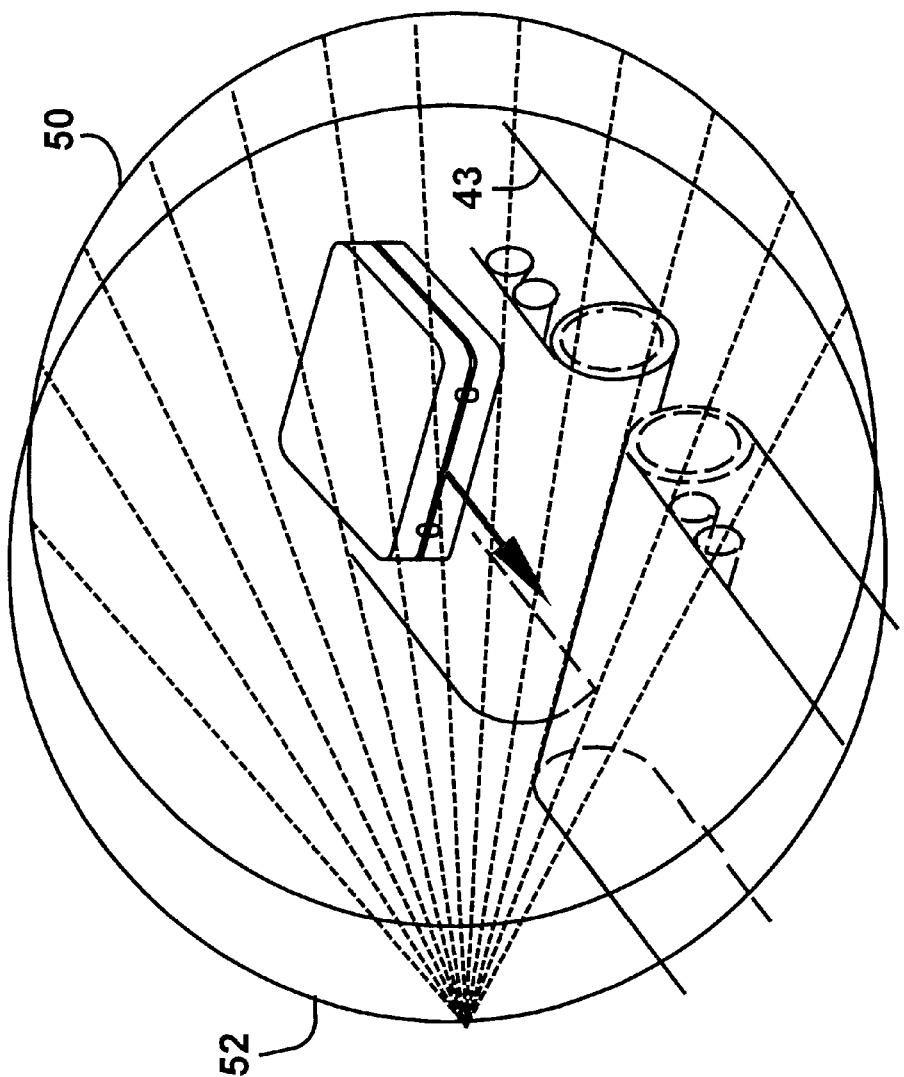
FIG. 3A is an illustration of the automatic recognition system of FIG. 3 shown in use in conjunction with a baggage inspection station.

FIGS. 3 and 3A illustrate another embodiment of the source and detector elements suitable for an application where the size of the apparatus is not a major concern. In this embodiment, the source array 52 and detector array 50 are configured as two co-axial rings of substantially equal diameter with the counterpoint Cs of one array offset axially, longitudinally a short distance from the counterpoint Cd of the other array. The distance between source array 52 and detector array 50 is exaggerated in FIG. 3 to illustrate the configuration of each ring. This geometry has the advantage of broader coverage for each source in comparison with the first embodiment of FIG. 2 because of the larger distance between source and object. Also, the scan space is evenly covered by X-ray beams in this embodiment because of its symmetry.

Figure 4:
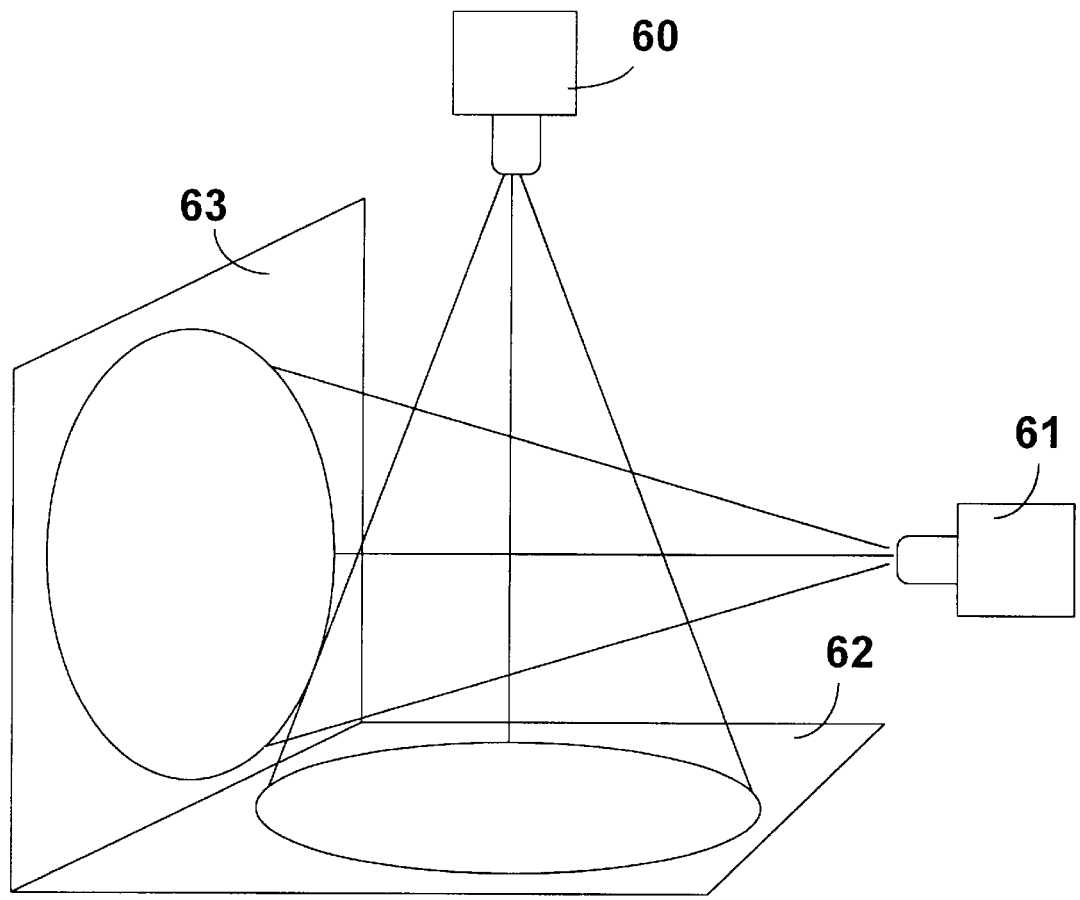
FIG. 4 is a schematic representation of another embodiment of the present invention.

In other applications, particularly the manufacturing arts, the object to be scanned may be uniform in shape, composition, or both. True tomography may be replaced with pseudo tomography by employing a priori knowledge of manufactured components, their geometry, position, and material composition, as constraints in the algebraic reconstruction equations. In such situations, reduced system cost and faster computational speed can be achieved using a source and detector embodiment as illustrated in FIG. 4. Here, two sources 60 and 61 are used with two detector planes 62 and 63. Although greatly simplified in comparison to the other embodiments of FIGS. 1–3A, the techniques of the present invention can be used in this and similar embodiments.

Figure 5:
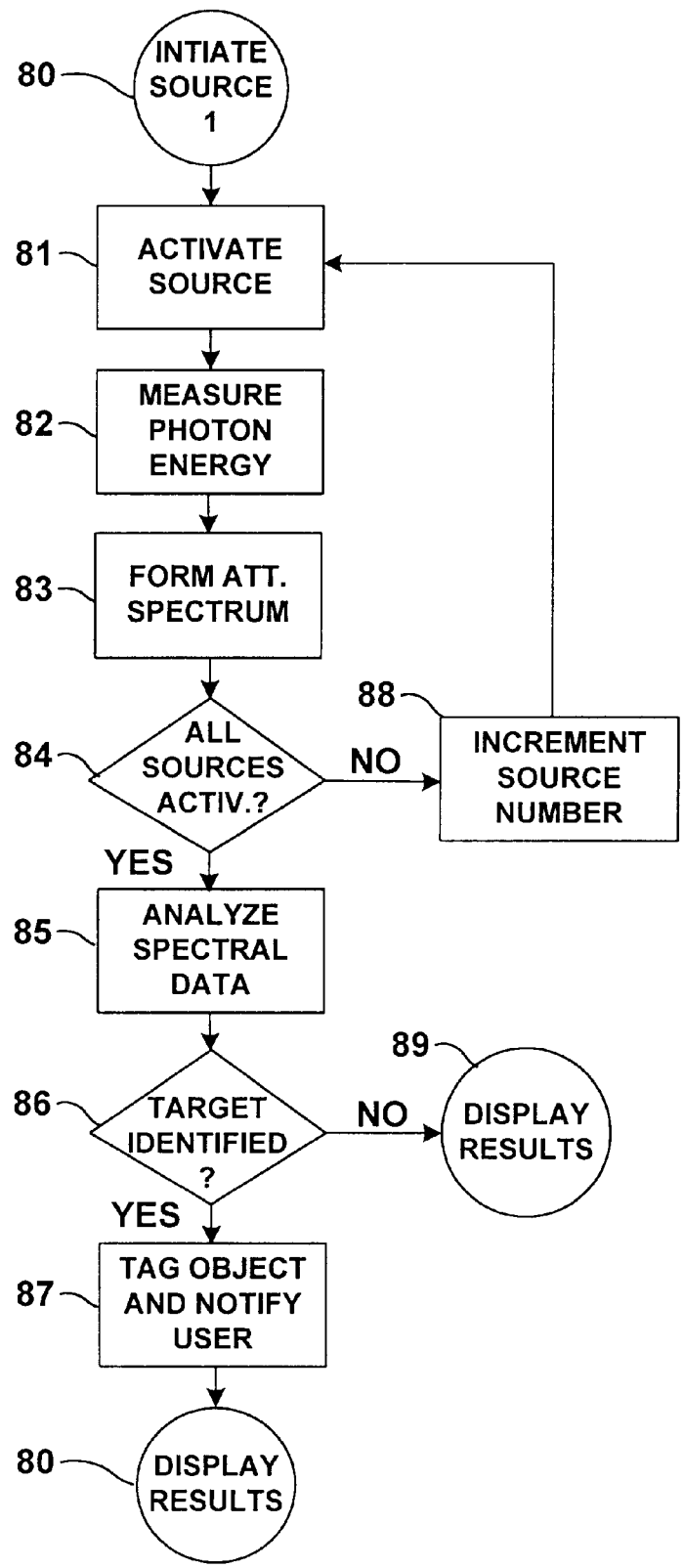
FIG. 5 is a flow chart depicting the major steps in carrying out the present invention.

Having provided an overview of suitable hardware elements to be used in accordance with the present invention, attention presently turns to the processing steps to be executed on the hardware. Turning to FIG. 5, the major steps in carrying out the present invention are illustrated as a flowchart. The process begins with initiation of the first source in step 80. The source is activated in step 81 to generate a beam of photons directed towards the object to be scanned. The energy level of the photons after traveling along the beam path is then measured in step 82. In step 83 spectral data are formed from the measured energy levels by counting the number of photons within certain energy ranges absorbed by each detector during a specific time increment. In step 84 the source number is checked to determine if all sources have been activated. If not, process step 88 is performed to increment the source number and return to step 81. If all sources have been activated, then process step 85 is performed to analyze the spectral data. In this way, steps 81–83 are repeated for each X-ray source in a plane.

The results from the above steps are used to form and analyze multispectral CT data in step 85 as discussed below. These data are then compared to data representing known targets of interest in step 86 to determine if one or more targets of interest are present. If not, an appropriate message is displayed in step 89 along with an enhanced X-ray or CT image for operator viewing. If one or more targets are identified in step 86, then the container is tagged or sorted in step 87 and an enhanced image is displayed in step 90 with a unique color or texture to identify the targets along with an appropriate text message to the operator.

Figure 6:
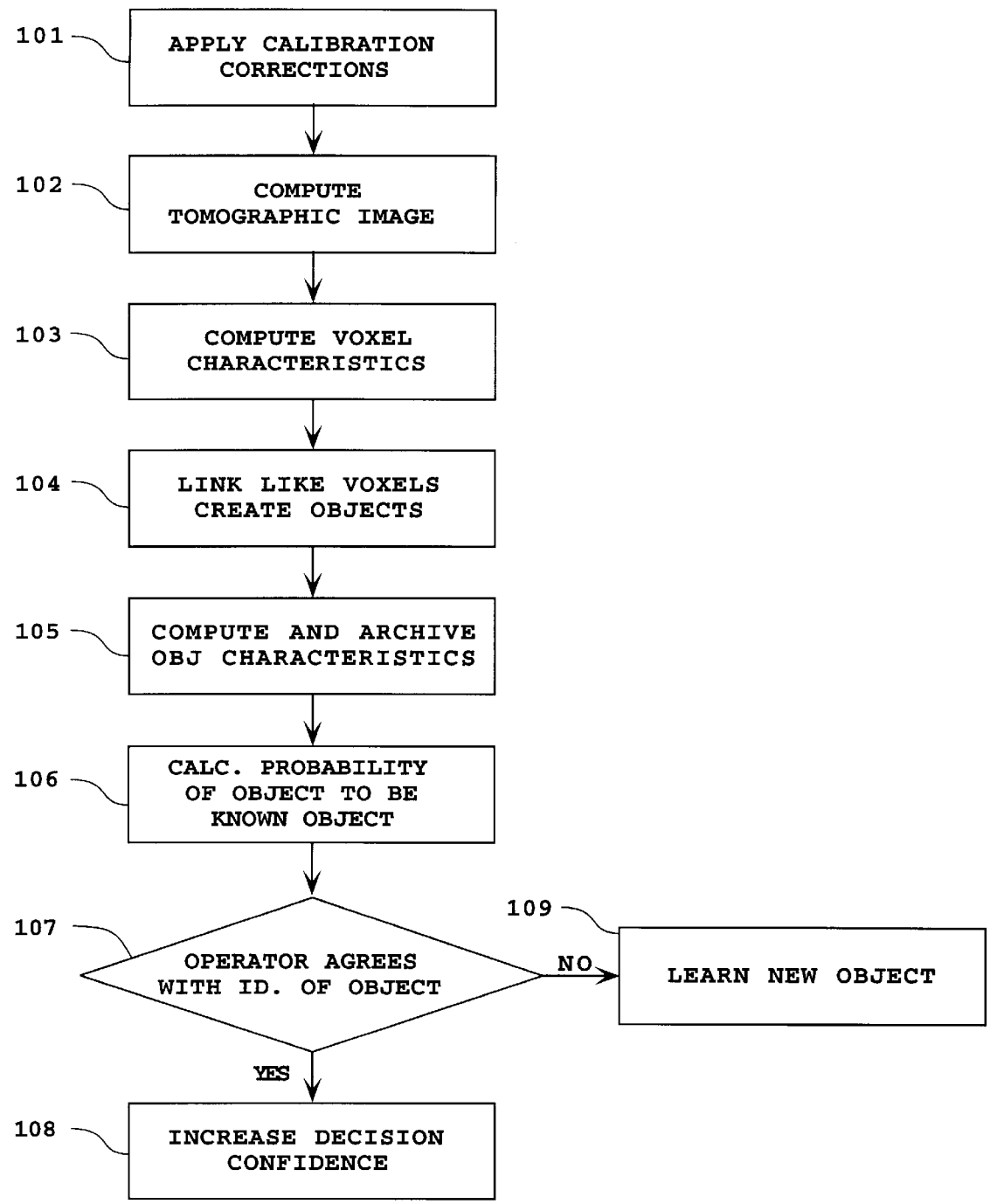
FIG. 6 is a flow chart detailing the steps of analysis spectral data and target identification in the process of FIG. 5.

The processing steps used to analyze the spectral data (step 85) and to identify the target (step 86) are illustrated in greater detail in FIG. 6. Spatial variation in source and detector element position, detector element effective area, and energy resolving differences between detector elements are corrected in step 101 before CT reconstruction occurs, i.e., $I_0/I$ is calculated. Correction is applied directly to the signal output of each detector element.

A CT algorithm is applied to each of the spectral data sets in step 102, resulting in multispectral attenuation data for each voxel comprising the object space. After calibration correction and CT reconstruction, the various spectral images are combined in step 103 to obtain relative attenuation at each voxel. This operation may include removal of particular artifacts arising from the mathematical reconstruction process. A voxel is now characterized by its attenuation of x-rays in each energy band. A matched filter is applied on a voxel-by-voxel basis in step 103 to determine the statistical likelihood or probability of a match to voxels of known targets of interest. These results represent the probability that a particular voxel contains a particular material determined by comparing the calculated attenuation data with attenuation data previously determined for targets of interest. Because this comparison is made for each of several targets, each voxel may have several possible matches with varying levels of probability.

In step 104 contiguous or near contiguous voxels with similar matches as determined in step 103 are linked together to be treated as a single material or an object for further analysis. It should be noted that in step 103 the voxels could have had high probability of being one of several materials. Steps 104 and 105 are repeated for each of the possible materials. In step 105 the material's shape, size, texture, fractal dimension, average absorption by energy band, and other characteristics are calculated and archived. The calculated characteristics are fed into an artificial neural network in step 106. Complex objects can be composed of several materials. Step 106 may involve several neural networks configured so that a second or subsequent neural network can treat a combination of materials in close proximity as a single object. For example, an orange is composed of pulp, seeds and skin all of which would be different materials but combined to form one object. A purely statistical algorithm using matched filter algorithms could be used in place of or in addition to the neural network. The object identity along with a measure of the certainty of identification is calculated and displayed to the operator.

In step 107, the operator has the opportunity of confirming the decision made in step 106. If he agrees with the decision, his positive response is used in step 108 to increase the confidence factor used by the system for future decisions. If he disagrees step 109 can be executed in which the object is given a name and its characteristics may be used for teaching the neural network about the new object.

If step 106 identifies the object with a high probability, the result is displayed by interface 7 with the object marked as identified. Interface 7 allows the person to mark the decision as correct or incorrect. If marked correct, the processor increases its "confidence factor" for that object's characteristics and adds the characteristics as an exemplar for retraining. If incorrect, the processor decreases its "confidence factor" for that object's characteristics.

Processor 4 is programmed such that the system will operate with an untrained or partially trained neural network. The invention includes the ability to train the neural network continuously or sporadically as needed for new objects. The neural network must be trained for each object to be identified. Training is done by presenting to the neural network the characteristics of an object and its name. The exact training process differs with the type of neural network used. Several standard neural network algorithms are possible and are well documented in the literature. Alternately, a pure statistical algorithm, such as the well known lest squares fitting, can be used in place of a neural network.

If step 106 does not identify the object or results in only a low probability of an identification, the characteristics are archived and the object is marked as unknown. The operator may then resolve the identification of the object. In step 109 the resolved identification and archived data are feed into processor 4 as the object's identification and an exemplar. If the identification is the same as one already known to the processor, then the processor combines the new exemplar with previously archived exemplars of the object and retrains the neural network using the combined exemplars. If the identification of the object is unique, the processor adds the object's identification and characteristics into its data base as a new object with one exemplar.

In step 102 the relative attenuation data from the different spectral bands is fused or combined to form a single image for operator viewing. This image is enhanced in step 106 with information from the analysis of steps 104–106. For example, highly correlated voxels can be illustrated in the image with a common color or texture to assist in operator viewing of the information. The results of the above analysis are displayed as a text message and as an enhanced graphic image in step 106.

Figure 7:
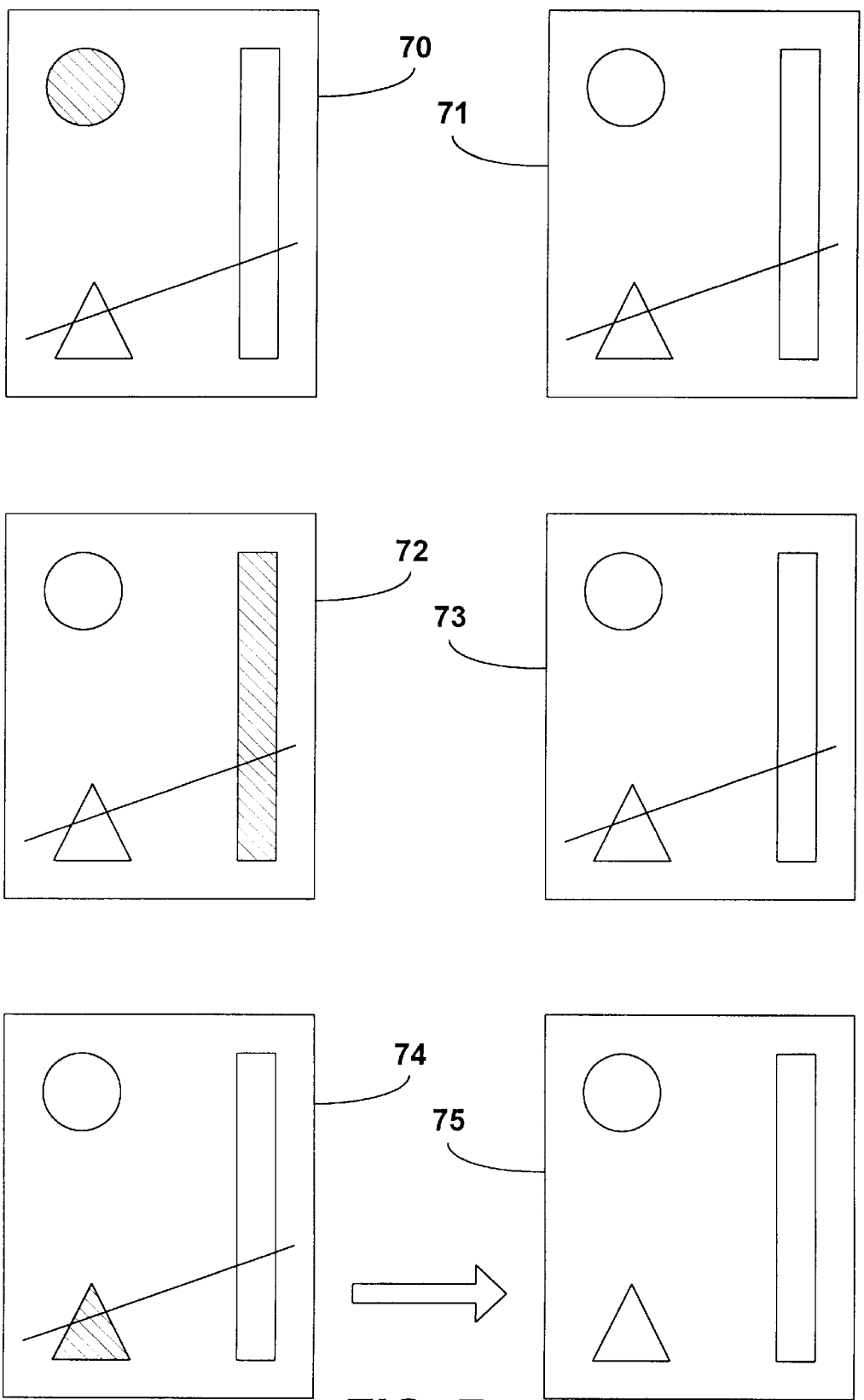
FIG. 7 is an illustration depicting the use of the process and system of the present invention to produce an enhanced image.

Turning to FIG. 7, the processing of multispectral data to form an enhanced image with a greater signal-to-noise ratio is illustrated. Images 70, 71, 72, 73, 74 correspond to the five energy ranges discussed above. The images 70–74 contain three objects represented by a circle, rectangle, and triangle, and an artifact represented by a line. While the line appears uniformly in all five images 70–74, the other three objects appear with varying intensities. This simulates a key difference between actual objects in the scanned image and artifacts caused by the finite number of detector elements, the finite number of sources, defective detector elements, and similar limitations of the apparatus and processing methods. In many cases, the attenuation values of actual objects within the scan space will vary with intensity level of the X-ray source while the artifact will have an attenuation value independent of energy level. The circle, rectangle, and triangle shown in images 70–74 simulate the variation of attenuation that different materials can have with varying X-ray source intensities. Thus, the circle is best resolved at the energy level of image 70, while the rectangle is best resolved at the energy corresponding to image 72 and the triangle at the energy level of image 74.

The fusing process in the present invention is used to both eliminate the artifacts represented by the line in images 70–74 and to produce a single enhanced image 75 that includes a clear picture of all three objects. The first step in this fusing process is to subtract one of the images, say 71, from the other four images 72–74 to eliminate artifacts in the image data. Because the artifacts, as represented here by the line, do not vary in intensity from one image to another, this differencing technique effectively eliminates the artifacts from the resulting images. These four images are then summed to produce an enhanced image 75 that includes unique colors, numerical values, or other distinguishing qualities assigned to identify the objects. Since the multi-spectral data are collected electronically by the MCA's 3 of FIG. 1, this process is performed numerically in the present invention. The final image 75 may be used to display results to an operator and for subsequent processing, including shape, wavelet, fractal or other techniques of image data analysis.

A number of advantages of the present invention are evident from the above description. First, the invention provides a means and apparatus for automatic detection of concealed objects with or without operator involvement. Small quantities or features of a target of interest concealed within an object may be detected. The invention provides for high throughput of objects during scanning operations without compromising detection capability. CT data are obtained using a compact and stationary X-ray source and detector array. An enhanced X-ray image, CT image, or both are provided for operator viewing. Statistically based confidence levels for target identification may be used based upon the data stored within the system, and a continuous learning capability is provided for improving target identification with system use.

The foregoing description of specific embodiments of the present invention have been presented for purposes of illustration and description. They are not intended to be exhaustive or to limit the invention to the precise forms disclosed, and obviously many modifications and variations are possible in light of the above teachings. For example, the number and arrangement of X-ray sources and detectors can vary considerably depending on the application. Where space constraints are not a factor, the sources can be moved away from the detectors resulting in greater coverage per source thus reducing the number of sources required. Also, the number and sophistication of data processing steps can vary greatly depending on the target identification resolution needed for a particular application. CT processing, for example, may be unnecessary where objects in the scan plane are relatively thin and homogeneous. The same holds true for shape, size, and texture analysis: in some applications a voxel-by-voxel comparison will provide sufficient discernment capability, in other applications shape, size, or texture analysis may be required to meet target identification requirements.

The embodiments illustrated and described above were thus chosen to best explain the principles of the invention and its practical application, thereby enabling others skilled in the art to best utilize the invention and various embodiments with various modifications as are suited to the particular use contemplated.

What is claimed is:

1. A system for identifying an object, comprising:

a substantially L-shaped source array comprised of a plurality of photon emitting elements for producing a plurality of x-ray photon beams directed towards the object, each photon beam being in a known energy band;

a substantially L-shaped photon energy measuring detector array including a plurality of detector elements and positioned relative to said source array, such that the object is located between said source array and said detector array, for measuring an energy of individual photons transmitted along said photon beams through the object;

a multi-channel analyzer circuit responsive to said detector array for determining said energy range of each photon energy and counting the number of photons per energy range per detector element per time interval, in order to generate multiple energy spectral photon counts;

computed tomography for constructing a spectral transmission by voxels of the object based on said multiple energy spectral photon counts;

a processor for isolating voxels with a predetermined spectral transmission, evaluating a connectivity of isolated voxels, and grouping interconnectible isolated voxels; and wherein said processor further includes a device for determining attenuation coefficient values of known materials and a device for the application of a matched filter to compare said attenuation coefficient values with those of the object, and wherein said processor further includes a device for fusing attenuation coefficient values of neighboring voxels and a device for linking and analyzing voxels having approximately similar attenuation values.

2. A system as recited in claim 1, wherein said source array and said detector array include a plurality of x-ray sources and detector elements, respectively.

3. A system as recited in claim 1, further including a device for learning a new set of parameters to be used in subsequent target identification.

* * * * *